United States Patent
Sakaguchi

(10) Patent No.: US 8,731,367 B2
(45) Date of Patent: May 20, 2014

(54) IMAGE PROCESSING APPARATUS

(75) Inventor: Takuya Sakaguchi, Shioya-gun (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1157 days.

(21) Appl. No.: 11/680,122

(22) Filed: Feb. 28, 2007

(65) Prior Publication Data

US 2007/0248319 A1 Oct. 25, 2007

(30) Foreign Application Priority Data

Mar. 1, 2006 (JP) .................. 2006-055291

(51) Int. Cl.
| | |
|---|---|
| *H04N 5/77* | (2006.01) |
| *A61B 1/04* | (2006.01) |
| *H04N 7/18* | (2006.01) |
| *H04N 9/47* | (2006.01) |
| *A62B 1/04* | (2006.01) |
| *A61B 1/06* | (2006.01) |
| *H04N 9/80* | (2006.01) |
| *G09B 23/28* | (2006.01) |
| *G06K 9/00* | (2006.01) |

(52) U.S. Cl.
USPC ............. 386/223; 386/224; 386/248; 348/45; 348/61; 348/64; 348/65; 348/69; 348/72; 348/74; 434/272; 382/128

(58) Field of Classification Search
USPC ........ 348/45, 61, 64, 65, 69, 72, 74; 386/223, 386/224, 248; 434/272; 382/128
See application file for complete search history.

(56) References Cited

U.S. PATENT DOCUMENTS

| | | | | |
|---|---|---|---|---|
| 5,034,987 | A | * | 7/1991 | Fujimoto et al. ............. 382/131 |
| 5,614,960 | A | * | 3/1997 | Chiba et al. .................. 348/700 |
| 6,047,080 | A | | 4/2000 | Chen et al. |
| 6,501,848 | B1 | | 12/2002 | Carroll et al. |
| 6,685,642 | B1 | * | 2/2004 | Garg et al. .................... 600/443 |
| 7,215,801 | B2 | * | 5/2007 | Bueno et al. ................. 382/128 |
| 2002/0111973 | A1 | * | 8/2002 | Maddalozzo et al. ........ 707/526 |
| 2002/0154801 | A1 | * | 10/2002 | Ohishi ......................... 382/132 |
| 2003/0123606 | A1 | * | 7/2003 | Mollus et al. ................... 378/42 |

(Continued)

FOREIGN PATENT DOCUMENTS

| | | |
|---|---|---|
| JP | 2-156778 | 6/1990 |
| JP | 2-266475 | 10/1990 |

(Continued)

OTHER PUBLICATIONS

U.S. Appl. No. 11/608,005, filed Dec. 7, 2006, Takuya Sakaguchi, et al.

(Continued)

*Primary Examiner* — Daquan Zhao
(74) *Attorney, Agent, or Firm* — Oblon, Spivak, McClelland, Maier & Neustadt, L.L.P.

(57) ABSTRACT

An image processing apparatus includes a storage unit which stores data of a plurality of medical images at different imaging angles or different imaging positions with respect to the same region, a display unit which displays the data of the medical image read out from the storage unit, and a control unit which controls the storage unit and the display unit to play back the plurality of medical images as moving images and pause playback of the medical image.

15 Claims, 17 Drawing Sheets

(56) References Cited

U.S. PATENT DOCUMENTS

| | | | |
|---|---|---|---|
| 2004/0066389 A1* | 4/2004 | Skyba et al. | 345/619 |
| 2005/0220264 A1 | 10/2005 | Homegger | |
| 2006/0210147 A1 | 9/2006 | Sakaguchi | |

FOREIGN PATENT DOCUMENTS

| | | |
|---|---|---|
| JP | 5-184576 | 7/1993 |
| JP | 7-79959 | 3/1995 |
| JP | 8-131429 | 5/1996 |
| JP | 10-99323 | 4/1998 |
| JP | 10-272136 | 10/1998 |
| JP | 2001-120547 | 5/2001 |
| JP | 2002-336222 | 11/2002 |
| JP | 2002-351293 | 12/2002 |
| JP | 2004-8304 | 1/2004 |
| JP | 2004-313545 | 11/2004 |
| JP | 2005-528157 | 9/2005 |
| JP | 2005-312775 | 11/2005 |
| JP | 2007-29487 | 2/2007 |
| WO | WO 2005/020155 A1 | 3/2005 |

OTHER PUBLICATIONS

U.S. Appl. No. 11/844,048, filed Aug. 23, 2007, Sakaguchi, et al.

Office Action issued Nov. 29, 2011, in Japanese Patent Application No. 2007-050701 (with English-language translation).

Office Action issued Jun. 12, 2012 in Japanese Application No. 2007-050701 (With English Translation).

Japanese Decision of Rejection issued Sep. 18, 2012, in Japan Patent Application No. 2007-050701 (with English translation).

Japanese Decision of Dismissal of Amendment issued Sep. 18, 2012, in Japan Patent Application No. 2007-050701 (with English translation).

Office Action mailed Sep. 10, 2013, in Japanese Patent Application No. 2012-179544 (with English Translation).

Office Action mailed Aug. 6, 2013, in Japanese Patent Application No. 2012-013931 (with English-language Translation).

Office Action mailed Jan. 7, 2014, in Japanese Patent Application No. 2012-179544 (with English-language Translation).

* cited by examiner

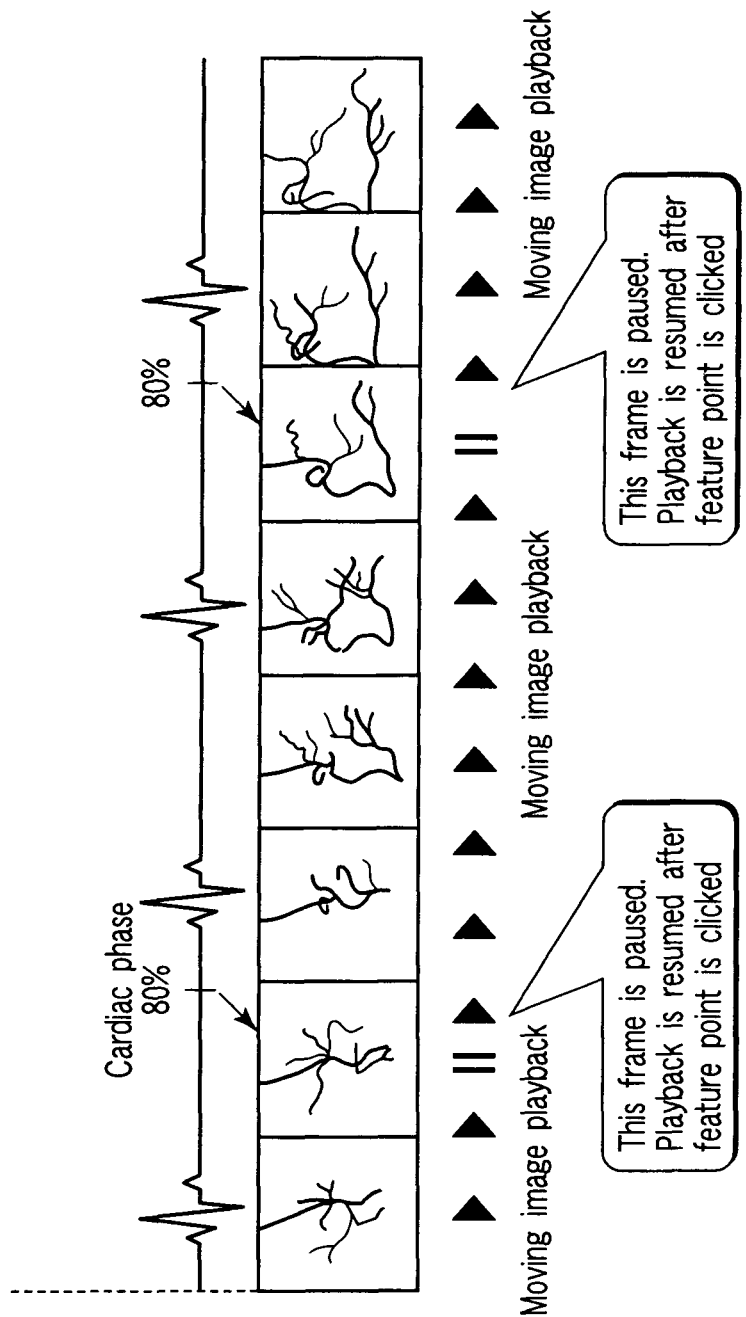
F I G. 1

Click marker

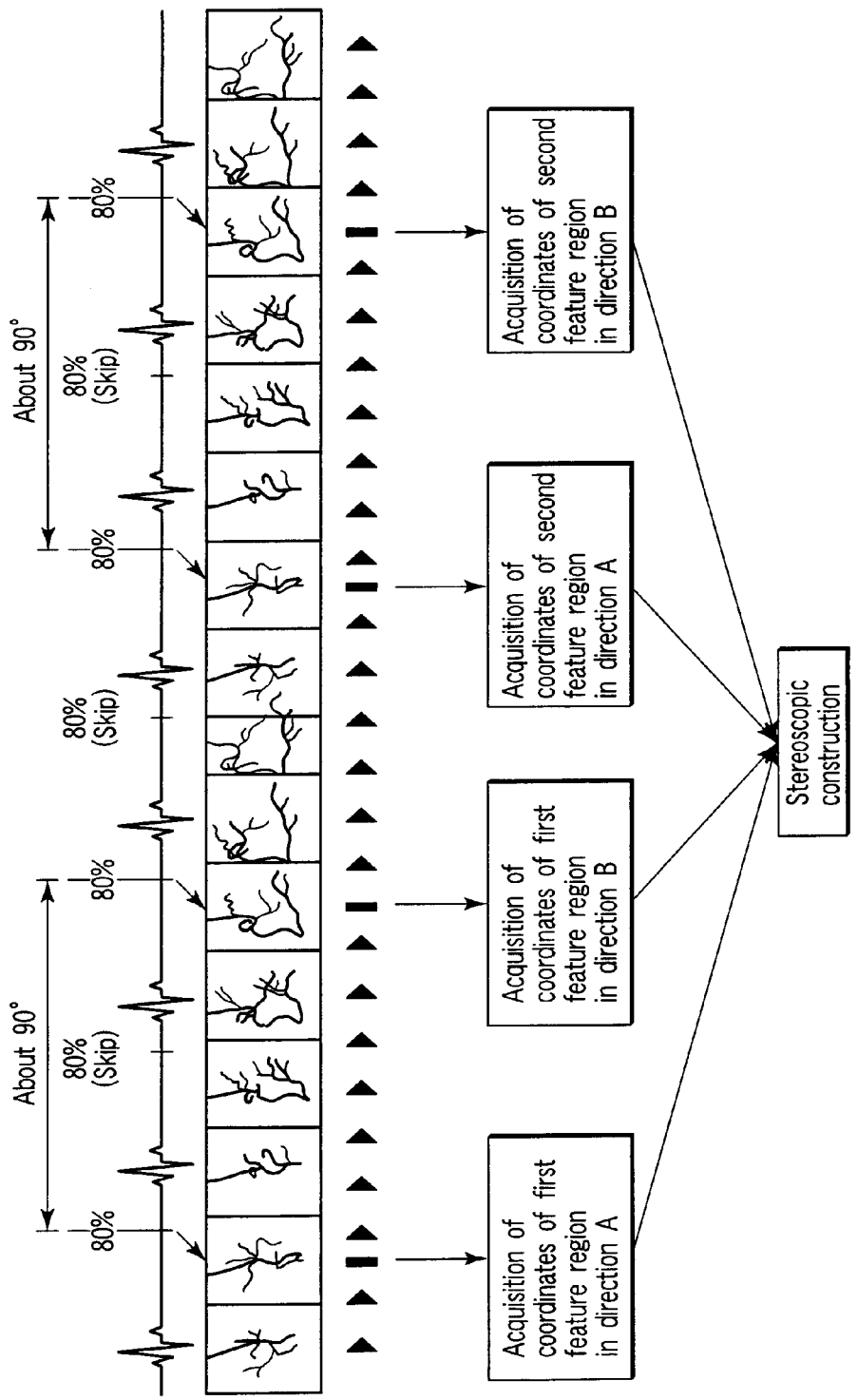
F I G. 5A

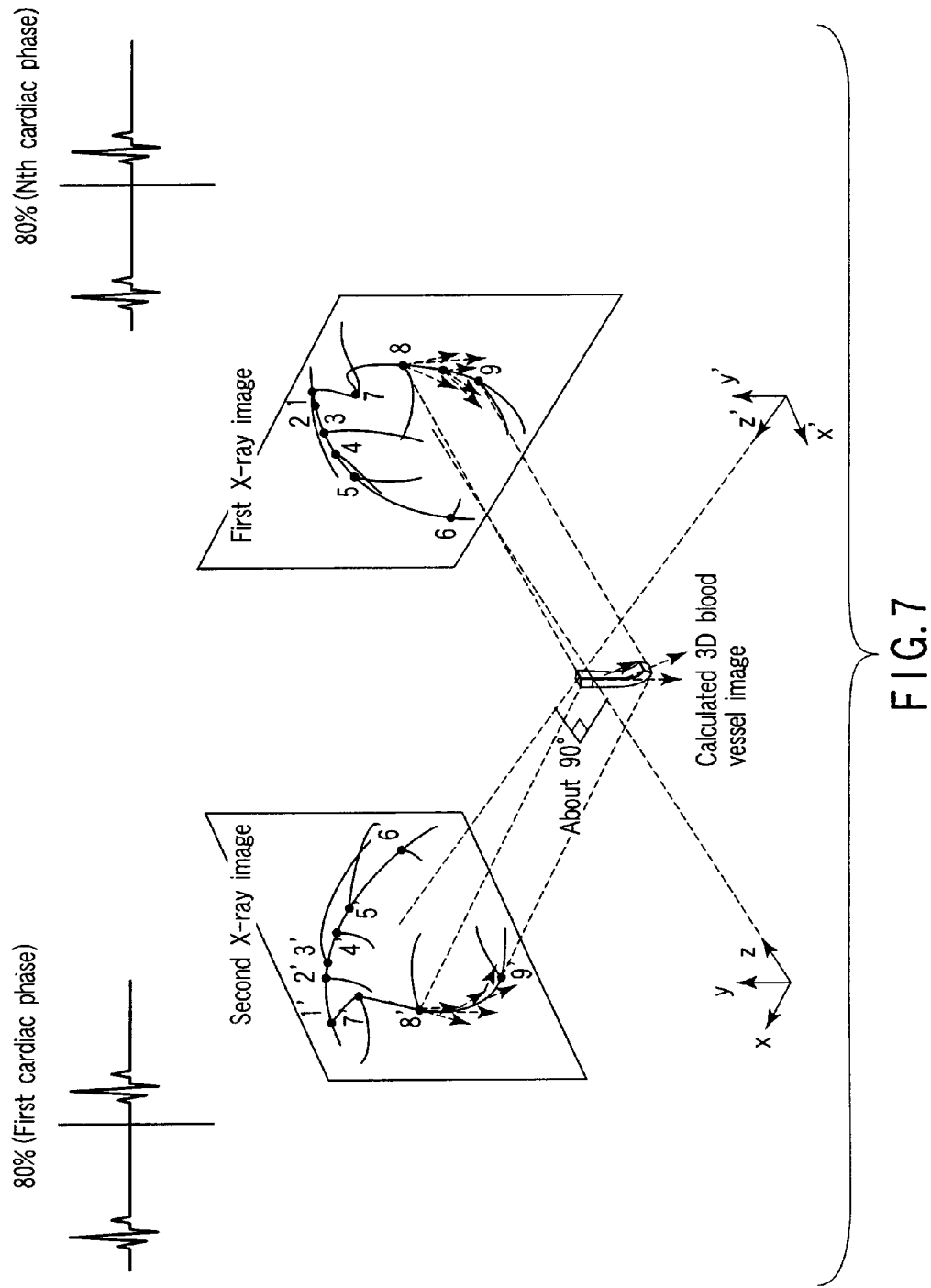
F I G. 7

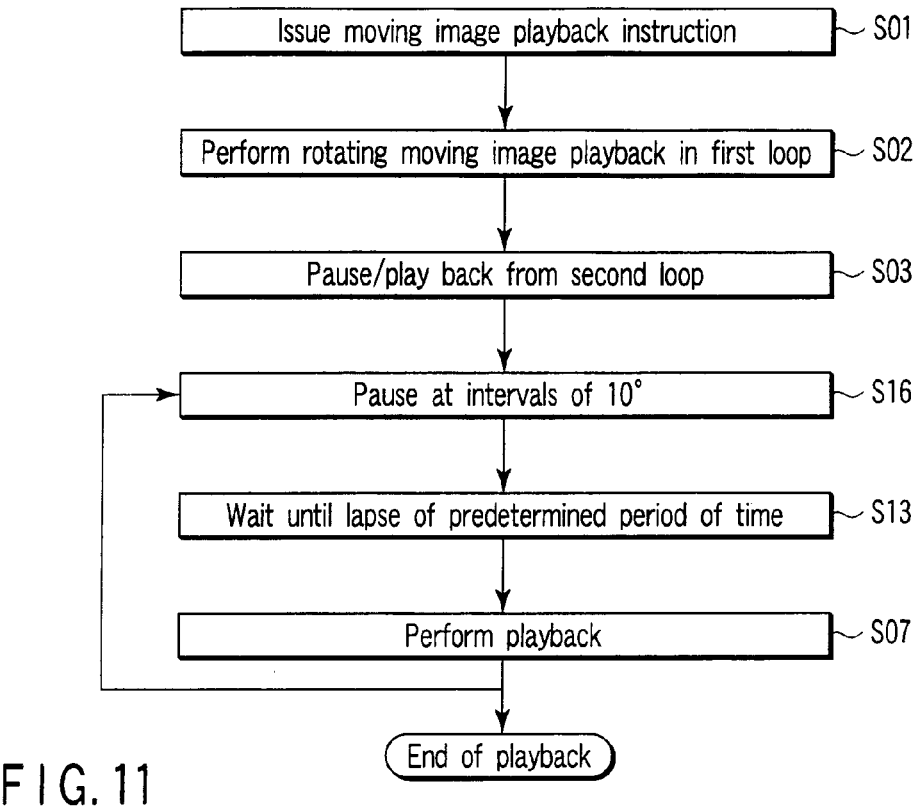
F I G. 11
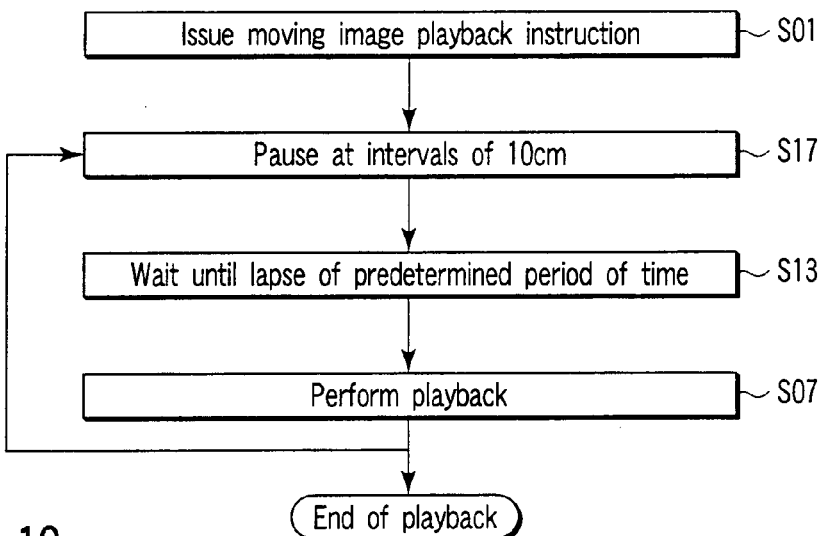
F I G. 12

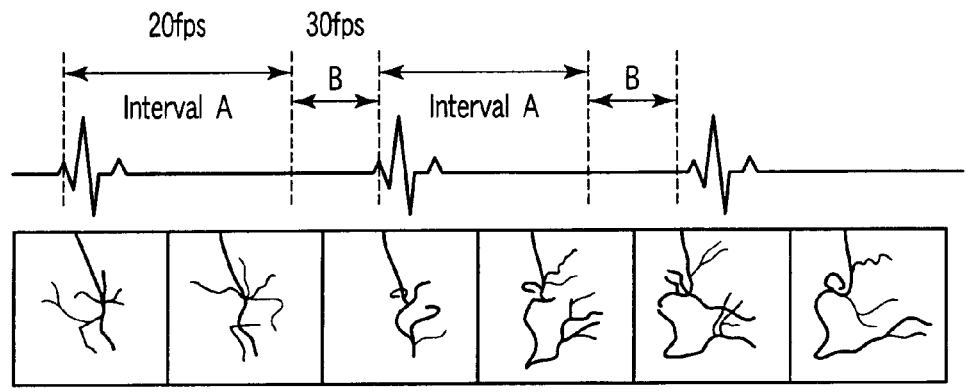
F I G. 15
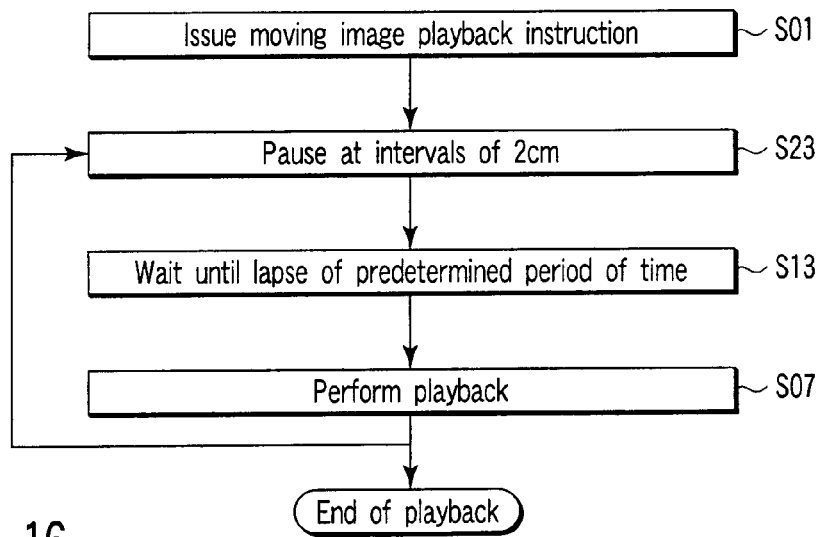
F I G. 16

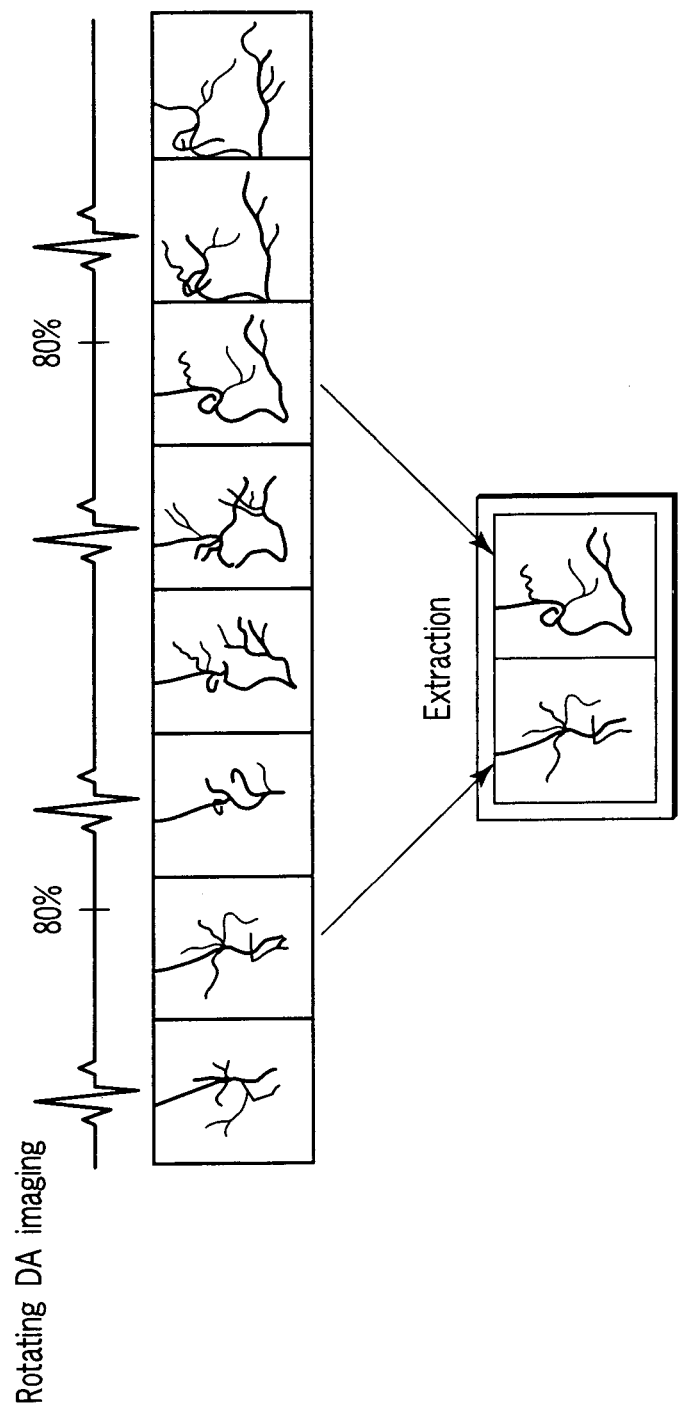
F I G. 20

IMAGE PROCESSING APPARATUS

CROSS-REFERENCE TO RELATED APPLICATIONS

This application is based upon and claims the benefit of priority from prior Japanese Patent Application No. 2006-055291, filed Mar. 1, 2006, the entire contents of which are incorporated herein by reference.

BACKGROUND OF THE INVENTION

1. Field of the Invention

The present invention relates to an image processing apparatus which generates and displays a stereoscopic image of a blood vessel or the like from a plurality of medical images at different imaging angles.

2. Description of the Related Art

As shown in FIG. 19, there is available a technique of designating a plurality of anatomically identical points from at least two medical images, typically X-ray images, at different imaging angles, and constructing a three-dimensional blood vessel image from the positional relationship between the designated points. These two X-ray images are preferably obtained in phase with the heart, as shown in FIG. 20. Images obtained in different cardiac phases differ in the three-dimensional positions of feature regions with the movement of the heart. This contradicts the major premise of the acquisition of a geometrical relationship, and hence makes it impossible to perform accurate stereoscopic construction.

As imaging methods, the following three techniques are mainly known:
a) performing imaging from one direction, rotating an imaging system, and performing imaging from another direction at a different time;
b) repeatedly performing imaging while continuously rotating an imaging system, as shown in FIGS. 21A and 21B; and
c) simultaneously obtaining two images by imaging at the same time using a biplane system having imaging systems of two systems.

The method c) is most preferable because it can perform imaging at the same time, but cannot be practiced by facilities which have no biplane system. The method a) is the most general imaging method.

The method b) is an imaging method which has recently attracted attention. This is because the method allows to simultaneously observe the stereoscopic structure of a blood vessel and its movement. The method allows to extract two suitable images from many images. The operator displays the two extracted images side by side in the same window and designates corresponding points.

According to the method b), blood vessel branches overlap depending on extracted images, resulting in difficulty in designating corresponding regions. When branches of a blood vessel run in a complicated manner as in the case of the left coronary artery, in particular, branches frequently overlap. An error in the designation of corresponding points leads to an error in the construction of a spatial geometrical relationship, resulting in a deterioration in the accuracy of a stereoscopic display image. See U.S. Pat. No. 6,501,848.

BRIEF SUMMARY OF THE INVENTION

It is an object of the present invention to improve accuracy in designating corresponding points even in a complex structure.

An image processing apparatus of the present invention comprises a storage unit which stores data of a plurality of medical images at different imaging angles with respect to the same region, a display unit which displays the data of the medical image read out from the storage unit, and a control unit which controls the storage unit and the display unit to play back the plurality of medical images as moving images and pause playback of the medical image.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view for explaining the actions and effects of an embodiment of the present invention;

FIG. 5A is a view schematically showing the procedure in FIG. 4;

FIG. 7 is a supplementary view for step S08 in FIG. 4;

FIG. 11 is a flowchart showing another playback procedure according to this embodiment;

FIG. 12 is a flowchart showing another playback procedure according to this embodiment;

FIG. 15 is a supplementary view for the overall procedure in FIG. 14;

FIG. 16 is a flowchart showing another playback procedure according to this embodiment;

FIG. 20 is a view showing images displayed upon feature point designation operation in the prior art.

DETAILED DESCRIPTION OF THE INVENTION

Figure 2:
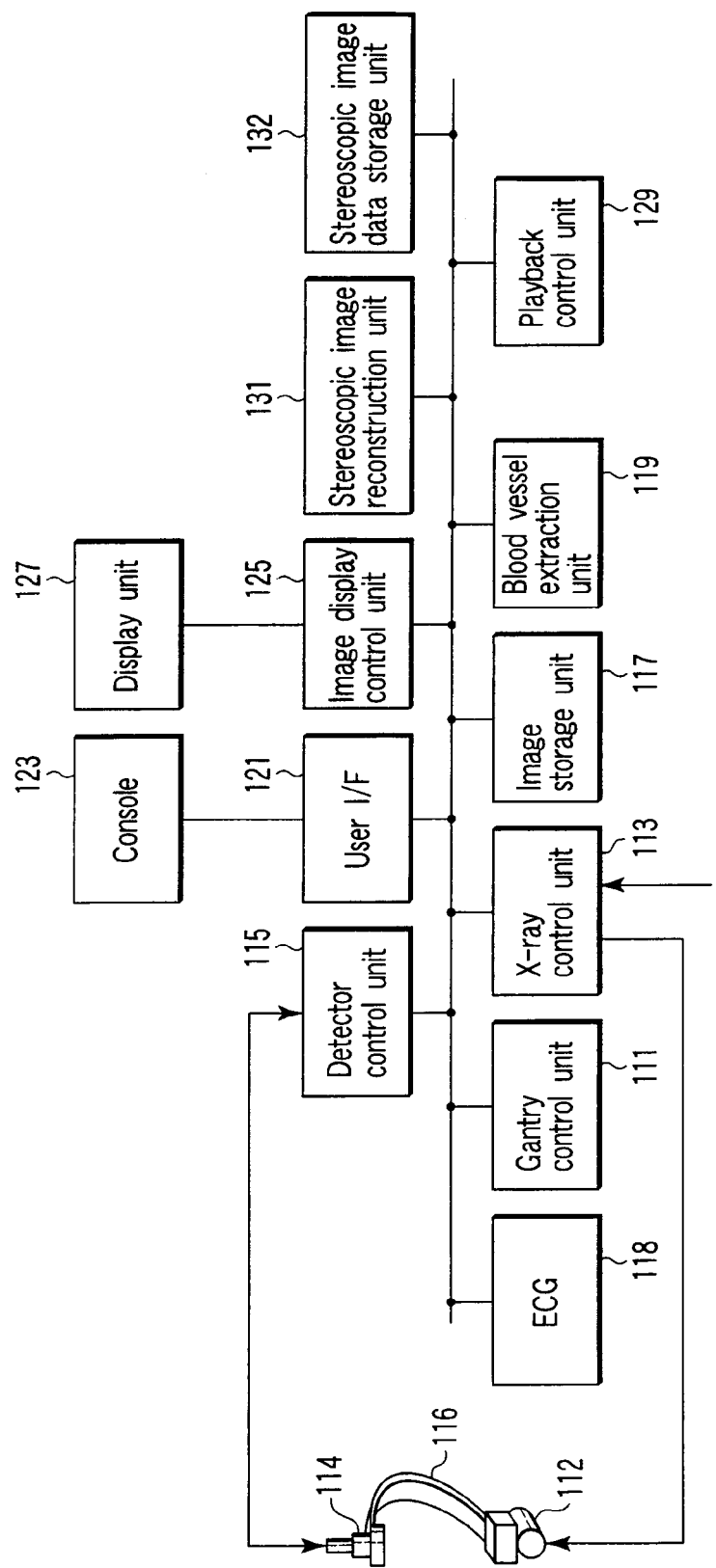
FIG. 2 is a view showing the arrangement of an X-ray diagnostic apparatus according to the embodiment.

An image processing apparatus according to an embodiment of the present invention will be described below with reference to the views of the accompanying drawing. The image processing apparatus will be described as an apparatus to be incorporated in an X-ray imaging apparatus. Obviously, however, this apparatus can be configured as a standalone apparatus. The image processing apparatus of this embodiment is an apparatus having a function of reconstructing a three-dimensional image from images obtained by imaging from at least two directions. The type of images and the like are not specifically limited.

This embodiment has a unique feature for improving accuracy in manually designating anatomically identical points (corresponding points) between images for each image even in a complex structure including intricate blood vessels and the like. As shown in FIG. 1, this apparatus plays back/displays a rotating moving image as a moving image at the same frame rate (1× speed) as that at the time of imaging, and pauses images according to a predetermined rule, typically at frames corresponding to a specific cardiac phase (e.g., 80%) to display them as still images. When the operator clicks a feature region, the apparatus resumes playing back/displaying images as a moving image again, pauses playback at a frame corresponding to the same cardiac phase, and stands by for the designation of a feature region by the operator. A human excels in tracking a feature region on a moving image. It is easier for a human to visually track the movement of a feature region by connecting two images or two images and their preceding and succeeding images as a moving image than by simply displaying the two images as still images side by side. That is, the operator can visually track a feature region while seeing a rotating moving image. This improves the accuracy in designating corresponding feature regions even if, for example, blood vessels overlap, as compared with the case of still image display. As a consequence, it can be expected to improve the image quality of a stereoscopic image.

The terms to be used in the following description will be defined below:

cardiovascular stereoscopic display: modeling a stereoscopic structure from projection information in a small number of directions by approximating (modeling) a blood vessel to an ellipse or polygon;

cardiac phase: a numeric value of 0 to 100% representing a cardiac cycle, which is generally calculated by dividing the period between the timing of an R wave in an electrocardiogram, which corresponds to 0, and the timing of the next R wave corresponding to 100 by 100;

same cardiac phase: the same (similar) cardiac phase (Typically, a detector performs imaging at a frame rate of about 30 fps (frames/sec), and can obtain images of about 30 frames/heartbeat, assuming that the heartbeat rate is 1/sec (60/min), and one image is obtained at intervals of one degree. Therefore, it is possible to check cardiac phases with a time resolution of about 100/30=3.33%);

end diastole: a time phase in cardiac motion in which the heart dilates and looks arrested. A time phase corresponding to a cardiac phase of about 70% to 80% is called a end diastole;

rotating imaging: "rotating" indicates rotating an imaging system (a pair of an X-ray and a detector) around a subject. This operation is also referred to as "pivoting". In general, a C-arm rotates at 30°/sec. Assuming that one imaging operation requires 180°, one imaging operation required six sec. Assuming that the heartbeat rate is 1/sec and this apparatus obtains one image at every 1° by imaging, the apparatus acquires medical images corresponding to six heartbeats, typically 180 X-ray images as X-ray image data, per imaging operation;

2D: a two-dimensional image. An X-ray diagnostic apparatus obtains a 2D image;

3D: a three-dimensional image;

biplane: an X-ray diagnostic apparatus including imaging systems of two systems, which can simultaneously perform imaging from two directions;

ECG: an electrocardiogram;

feature region: a region having a feature form of a region, e.g., a branch portion or narrowed portion of a blood vessel;

feature point: a point designated on a feature region;

loop playback: repeatedly playing back a series of temporally consecutive images as a moving image. After imaging, the operator often observes images by repeatedly playing back (looping) 90 frames of the images;

respiration: a process which causes the subject to move. Respiration has periodicity. A sensor is attached to a subject to grasp respiratory motion. In the case of MRI, a sensor may be attached to the nose;

IVUS: IVUS (Intra-vascular ultrasound) read as [áivˆs]; and three-dimensional image data: including the following two types A) and B). Type A) is three-dimensional image data mainly generated by CT or MRI. Obviously, volume-reconstructed data obtained by an X-ray diagnostic apparatus corresponds to three-dimensional image data of type A. Three-dimensional image data of type A) has values concerning all the voxels in a three-dimensional area. More specifically, for example, 134,217,728 values are provided for a three-dimensional area of 512×512×512. Type B) is three-dimensional image data given as vector amount (vector data) defining a three-dimensional area, and more specifically, comprises, for example, the center line coordinates and diameter of a blood vessel. A display apparatus paints an area corresponding to the center line coordinates and the diameter. The data amount of three-dimensional image data of type B) is much smaller than that of three-dimensional image data of type A.

Figure 3:
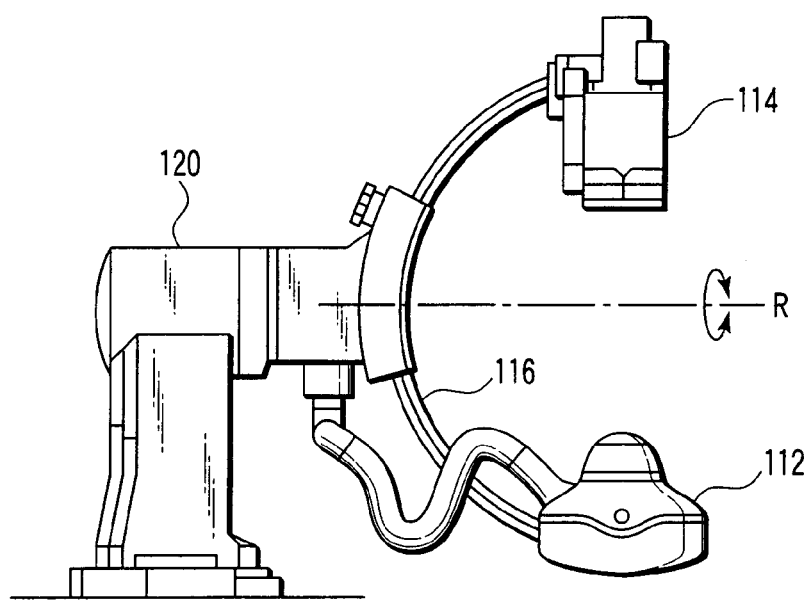
FIG. 3 is a side view of the imaging unit of the X-ray diagnostic apparatus in FIG. 2.

FIG. 2 shows an X-ray imaging apparatus incorporating the image processing apparatus according to this embodiment. The X-ray imaging apparatus has the gantry shown in FIG. 3. An X-ray tube 112 and an X-ray detector 114 are mounted on a C-arm 116. The X-ray detector 114 squarely faces the X-ray tube 112 through a subject P. The X-ray detector 114 is typically a flat panel detector comprising a two-dimensional array of detection elements (pixels) which directly or indirectly convert incident X-rays into electric charges. The X-ray tube 112 is mounted on one end of the C-arm 116 which is supported on a floor type stand 120 so as to be biaxially rotatable. The X-ray detector 114 is mounted on the other end of the C-arm 116.

The X-ray imaging apparatus equipped with the image processing apparatus according to this embodiment includes an electrocardiograph (ECG) 118 which measures the electrocardiogram of the subject and a gantry control unit 111. The gantry control unit 111 arbitrarily controls the imaging angle of the C-arm 116 and acquire data about the imaging angle from a sensor (not shown) in accordance with operator instructions from a console 123 connecting to the gantry control unit 111 through an interface 121. An image storage unit 117 stores the data about the imaging angle together with X-ray image data repeatedly generated from the X-ray detector 114 through a detector control unit 115 in synchronism with X-rays generated from the X-ray tube 112 upon application of tube voltages from an X-ray control unit 113, and cardiac phase data at the time of each X-ray imaging operation.

Figure 21A:
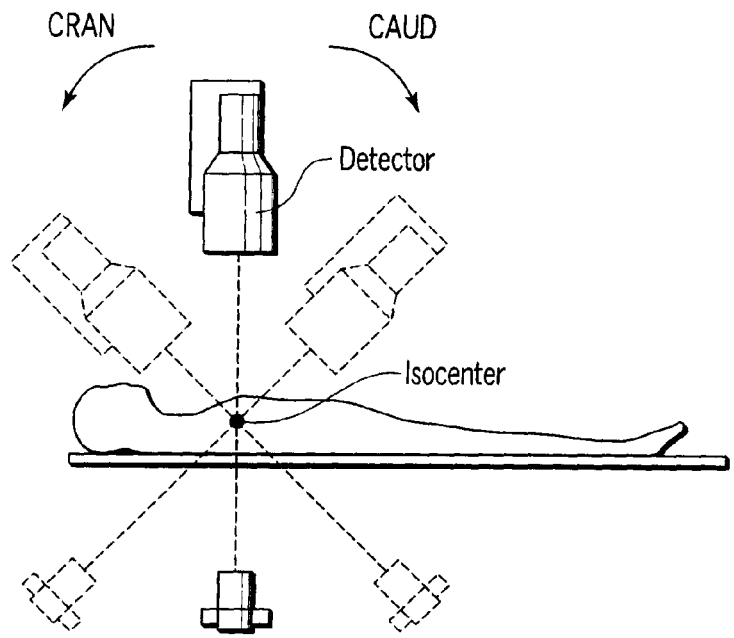
FIGS. 21A and 21B are views showing conventional rotating imaging operation.
Figure 21B:
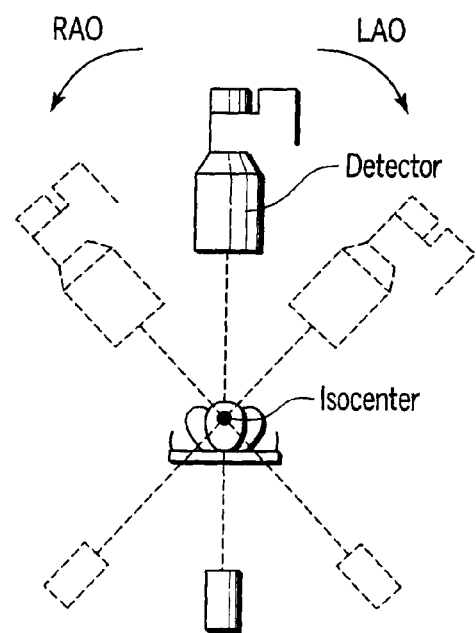

Performing rotating imaging like that shown in FIGS. 21A, 21B allows to acquire a plurality of X-ray images whose imaging angles continuously change at 30 fps throughout an angle range of about 180°. This imaging period typically has a time length of about 10 heartbeats.

A display unit 127 is a display apparatus such as a CRT, which connects to the apparatus through an image display control unit 125. A blood vessel extraction unit 119 extracts a contrast image of a blood vessel obtained by, for example, threshold processing from X-ray image data.

A playback control unit 129 controls the moving image display of the display unit 127 by controlling read operation of X-ray image data stored in the image storage unit 117. More specifically, the playback control unit 129 plays back the X-ray image data stored in the image storage unit 117 as a moving image at a frame rate (playback frame rate) of 30 fps equivalent to the frame rate (imaging frame rate) at the time of imaging operation, and pauses the display of the image at the time point when at least two X-ray images of a plurality of X-ray images which correspond to a predetermined rule during the playback period. Typically, the playback control unit 129 pauses the display of at least two X-ray images which correspond to a specific cardiac phase and have an imaging angle difference of about 90°. Note that the playback control unit 129 repeatedly plays back (loop playback) a plurality of X-ray images in the forward direction coinciding with the imaging sequence.

A stereoscopic image reconstruction unit 131 reconstructs the stereoscopic image data of the blood vessel image extracted by the blood vessel extraction unit 119 from each X-ray image on the basis of the positional relationship between a plurality of feature points designed on at least two X-ray images by the operator.

Figure 6:
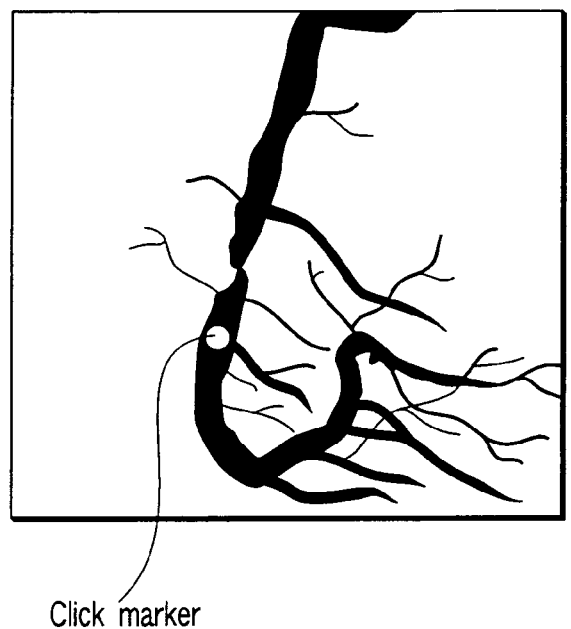
FIG. 6 is a view showing a click marker in step S05 in FIG. 4.
Figure 4:
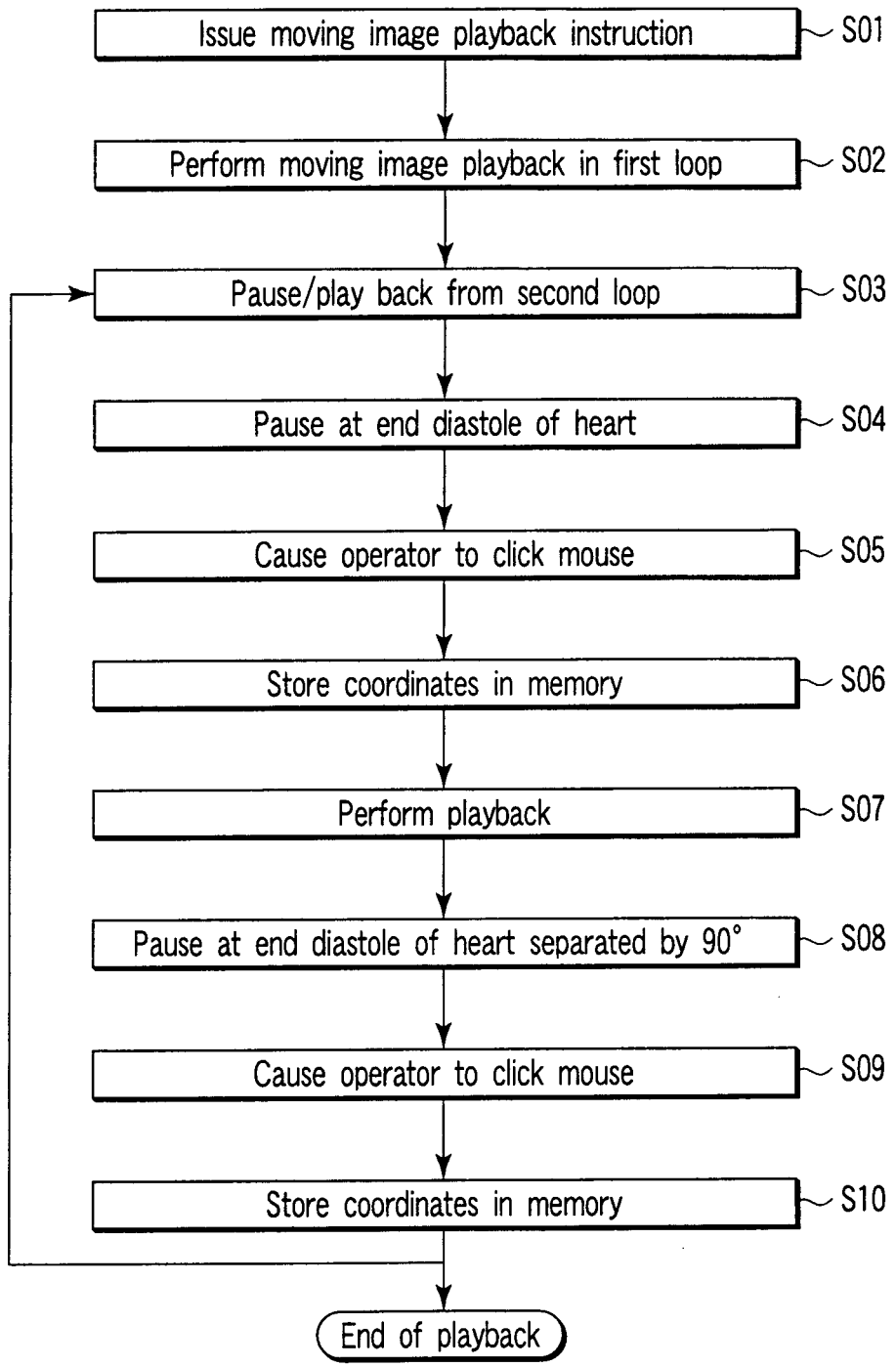
FIG. 4 is a flowchart showing a playback procedure according to this embodiment.

Moving image playback control performed by the playback control unit 129 to support feature point designating operation will be described with reference to FIGS. 4 and 5A. As shown in FIG. 4, the playback control unit 129 calls and plays back/displays a moving image file (still image group) designated by the operator from a list of stored X-ray image data files (S01). Assume that this moving image comprises a group of still images of 90 frames. In the first loop, the playback control unit 129 continuously plays back 90 X-ray images at the same frame rate (playback speed (1×)) as that at the time of imaging operation without pause (S02). Subsequently, in the second loop, the playback control unit 129 starts playing back 90 X-ray images in the forward direction from the first image, and pauses the playback/display of an X-ray image corresponding to a cardiac phase (e.g., 80%) at a end diastole of the heart as a specific cardiac phase which comes first (S03 and S04). As shown in FIG. 6, the operator clicks a feature region on the paused X-ray image by operating the mouse of the console 123 (S05). The image storage unit 117 or a memory (not shown) stores the data of the clicked image coordinates (S06). In response to clicking as a trigger, the playback control unit 129 resumes playing back/displaying with a predetermined time lag of about 1 sec (S07).

The playback control unit 129 pauses the playback/display of an X-ray image which corresponds to the same cardiac phase as that of the previously paused X-ray image and exhibits an imaging angle difference of about 90° with respect to the previously paused X-ray image, as shown in FIG. 7 (S08). In practice, the playback control unit 129 pauses the playback/display of an X-ray image exhibiting an imaging angle difference of 90°±10° with respect to the previously paused X-ray image. In addition, the playback control unit 129 skips pausing an X-ray image which corresponds to the same cardiac phase as that of the previously paused X-ray image but exhibits an imaging angle difference falling outside about 90° with respect to the previously paused X-ray image, and continues playback/display at 1×.

The operator clicks the mouse on one portion of the feature region (S09). The data of the clicked image coordinates is stored (S10). Upon receiving the click event, the playback control unit 129 resumes playback/display and returns to step S03. In the third loop, the playback control unit 129 pauses and plays back images in the same manner as described above. In this case, however, the playback control unit 129 stores, in the memory, the coordinates acquired at this time as the second feature region coordinates different from the previous feature region. Upon acquiring the feature region coordinates of a predetermined number of images, more specifically, at least two pairs of images, the playback control unit 129 stops the playback. A stereoscopic image reconstruction unit 131 constructs stereoscopic image data concerning the blood vessel area extracted by the blood vessel extraction unit 119. A stereoscopic image data storage unit 132 stores the constructed data of the stereoscopic image of the blood vessel.

Figure 5B:
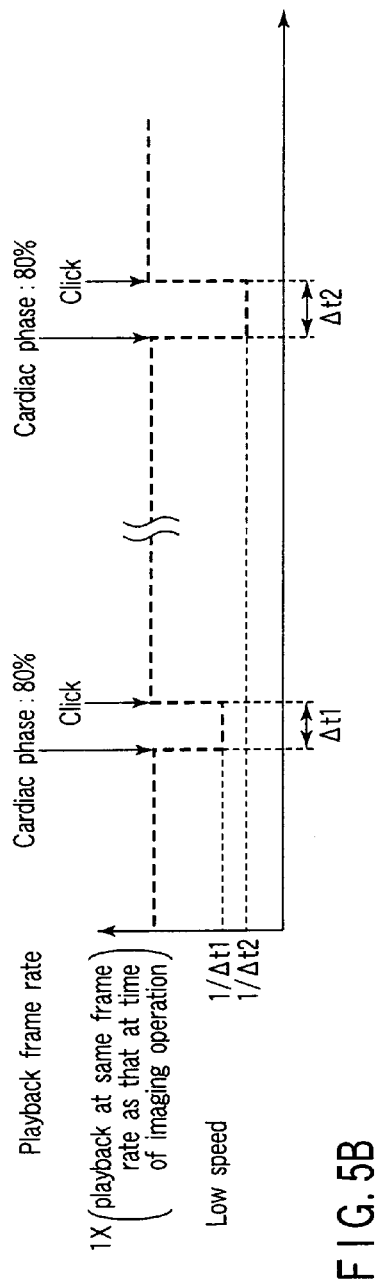
FIG. 5B is a view showing the operation in FIG. 5A from the viewpoint of a change in frame rate.
Figure 5C:
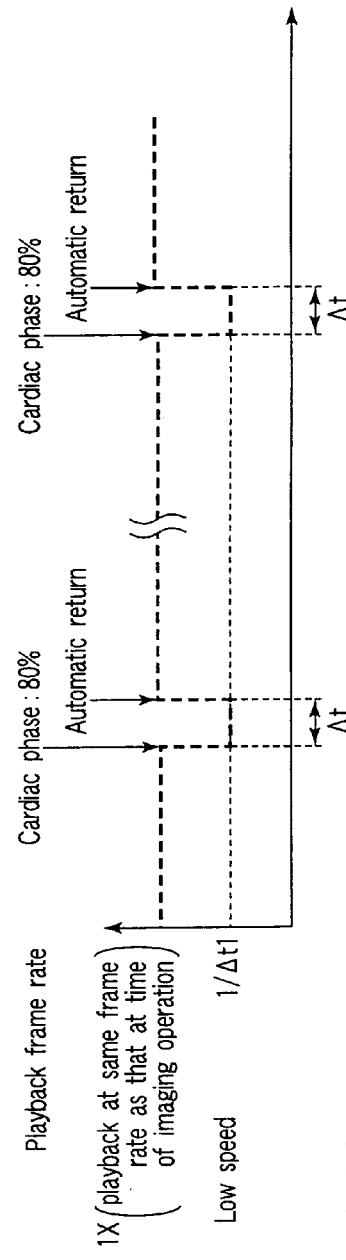
FIG. 5C is a view showing another operation in FIG. 5A from the viewpoint of a change in frame rate.

The above description has been made from the viewpoint of playback and pause. However, the present invention can be understood from the viewpoint of continuous playback and changes in frame rate. FIG. 5B shows temporal changes in playback frame rate. As shown in FIG. 5B, the playback control unit 129 starts playing back/displaying a moving image at almost the same frame rate (1×) as that at the time of imaging operation. The playback control unit 129 pauses the playback at a specific cardiac phase (e.g., 80%). Thereafter, when the operator clicks a feature point, the playback control unit 129 resumes 1× playback. Letting $\Delta t1, \Delta t2, \ldots$ be the period between the instant when the playback control unit 129 stops 1× playback and the instant when the operator clicks to resume 1×playback, the playback frame rate changes between the same frame rate as that at the time of imaging operation and a low frame rate $((1/\Delta t1, 1/\Delta t2, \ldots)$ obtained as the reciprocal of a pause period. Note that as shown in FIG. 5C, when playback is automatically resumed a predetermined period of time ($\Delta t$) after playback stop, the playback frame rate changes between the same frame rate as that at the time of imaging operation and $1/\Delta t$.

Repeating playback/pause in this manner makes it possible to accurately designate a feature region by using the human ability of tracking a feature region on a moving image. Therefore, it can be expected to improve the image quality of a stereoscopic image.

Note that a specific cardiac phase need not be a diastolic phase of the heart, and an arbitrary cardiac phase designated by the operator may be used. According to the above description, the operator designates one feature point at one pause. However, it suffices to designate a plurality of feature points. Assume that two points are to be designated. In this case, when the operator clicks the mouse on two portions, the playback control unit 129 automatically terminates the pause and automatically resumes playback/display after a predetermined time lag. In addition, the playback control unit 129 may resume playback when the operator presses the playback start button or a button on the keyboard instead of automatically resuming playback after mouse clicking. The operator may use an arbitrary device such as a touch panel other than the mouse. In addition, the imaging angle difference between X-ray images to be paused need not be about 90°, and can be arbitrarily designated. The number of loops (the number of times of repetitive playback) is arbitrary. That is, the playback control unit 129 repeats loops until the desired number of pairs of feature regions are obtained. For example, when the operator presses a specific key on the keyboard, the playback control unit 129 terminates playback.

Furthermore, a reference signal to be used is not limited to an electrocardiographic signal. It suffices to identify a cardiac phase in the same manner as described above from the periodic movement of the peak point of a line image obtained by projecting an X-ray image in one direction as "the periodic movement of a feature region on an image". It suffices to use a respiratory phase instead of a cardiac phase.

In addition, the number of directions (frames) in which images are to be paused is not limited to two. It suffices to pause X-ray images of three or more frames, of 90 frames, which satisfy a predetermined rule. Furthermore, it suffices to simply pause images in specific phases, e.g., all diastolic phases (80%), without setting any conditions concerning imaging angle differences. There is no need to set a single specific phase. It suffices to pause in two or more kinds of specific phases, e.g., all diastolic phases (80%) and all contraction phases (15%).

Figure 8:
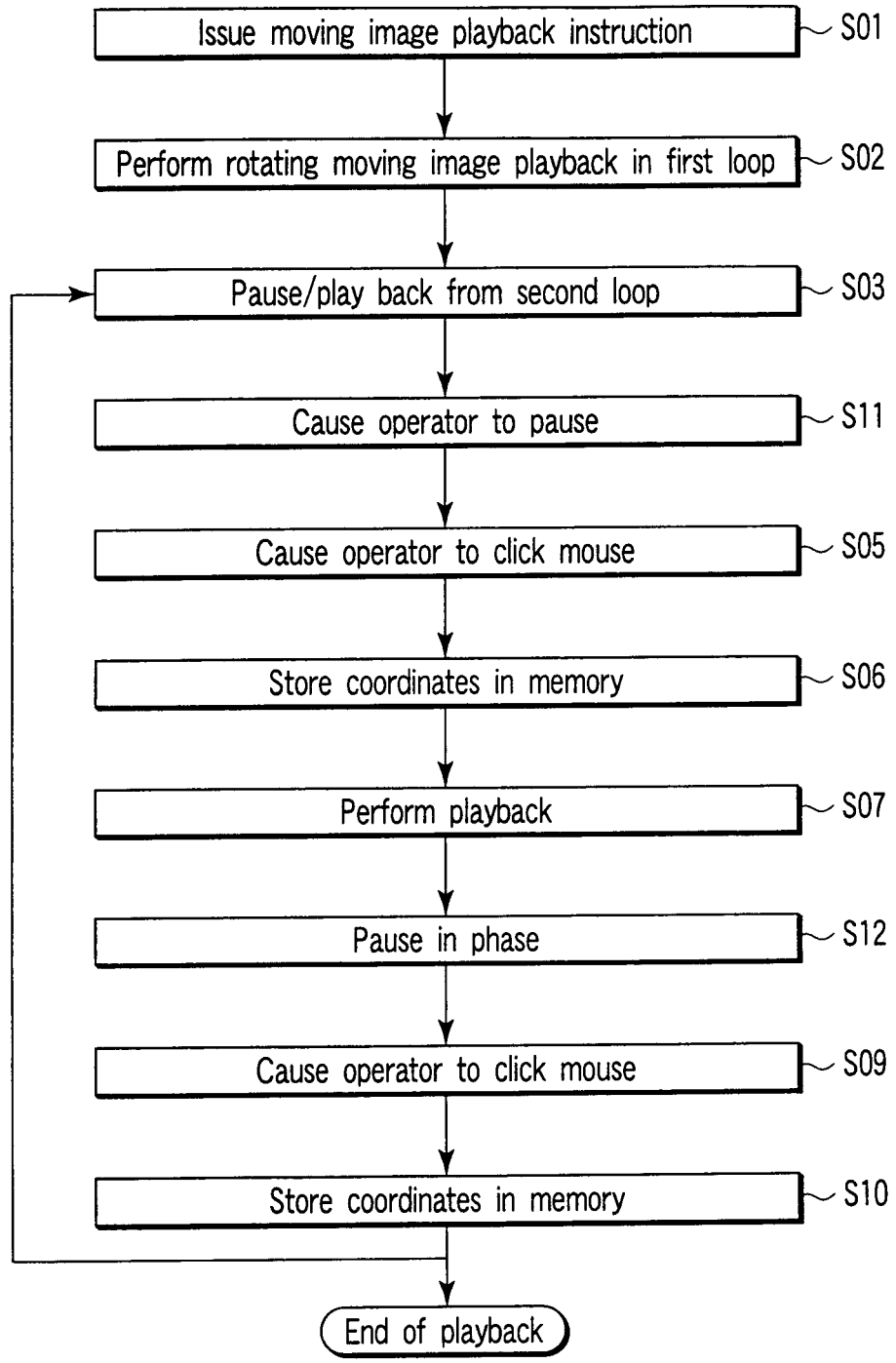
FIG. 8 is a flowchart showing another playback procedure in this embodiment.

As a specific cardiac phase, a diastolic phase (80%) of the heart may be set as a specified value. Alternatively, the operator may arbitrarily designate a specific cardiac phase in advance. Furthermore, as shown in FIG. 8, the operator may manually pause playback in the second loop (S11), and the playback control unit 129 may automatically pause playback in the loops from the second loop at the corresponding cardiac phase as a specific phase (S12).

Figure 9:
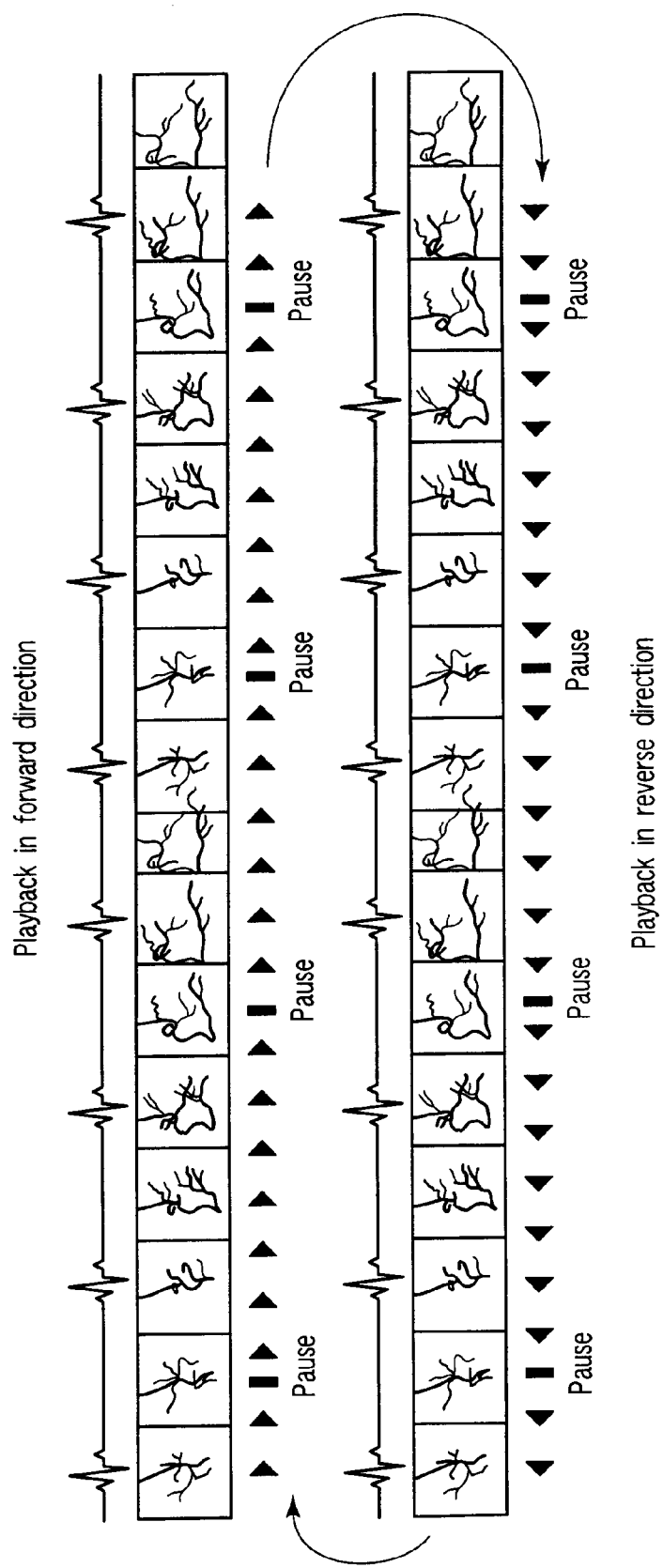
FIG. 9 is a view showing another playback loop according to this embodiment.

According to the above description, moving images are played back in the same forward direction as the imaging sequence, and this operation is repeated. As shown in FIG. 9, however, it suffices to play back moving images in the same forward direction as the imaging sequence, then play back moving images in the reverse direction, and alternately change the playback directions in this manner. This method allows the operator to observe motion from two directions, and hence improves the accuracy even if feature regions overlaps, because a human tries to interpolate.

In playback in the second or subsequent loops after the operator clicks feature points in steps S05 and S09, it suffices to display a click marker on a place where the operator clicks a paused image (for example, the marker is displayed in white, as exemplified by FIG. 6). This makes it easier for the operator to check, in reverse playback, whether the previously clicked place is correct.

Figure 10:
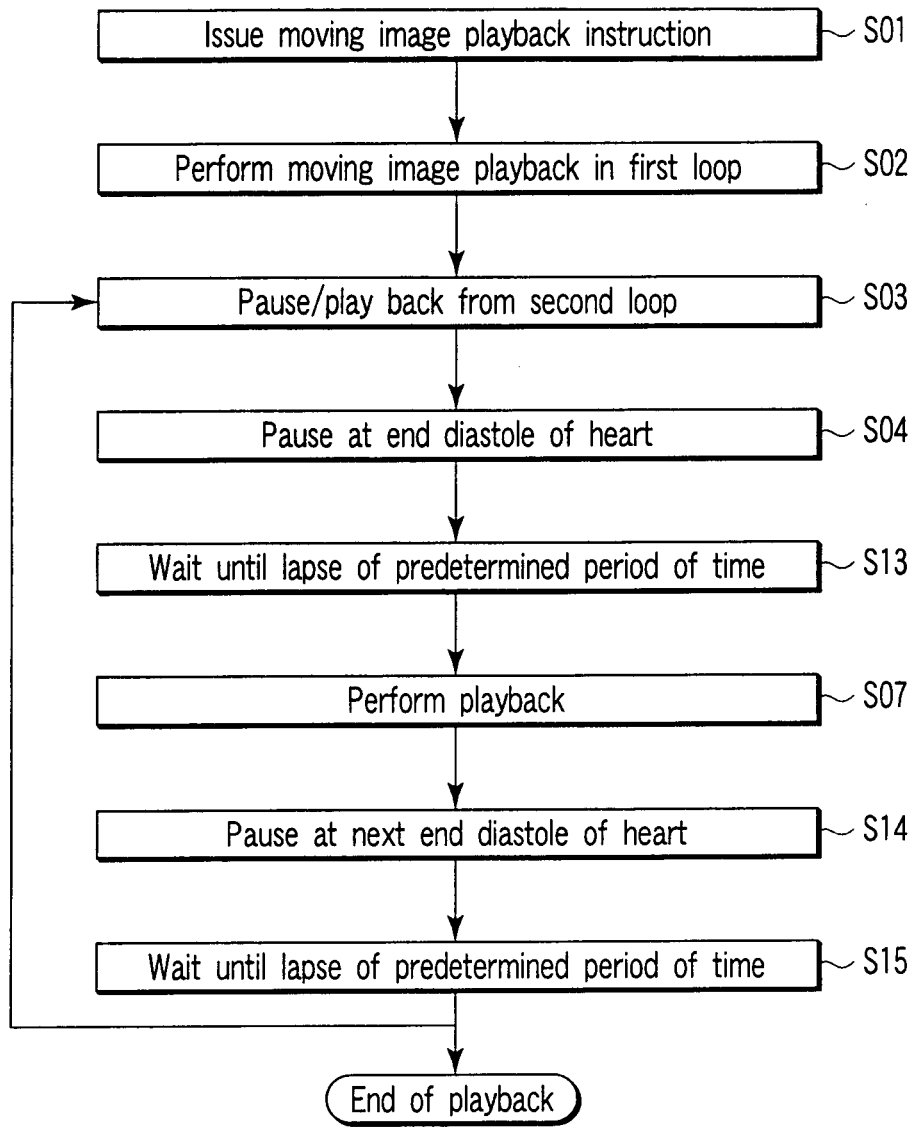
FIG. 10 is a flowchart showing another playback procedure according to this embodiment.

The above description has exemplified the feature point designating operation aimed at stereoscopic construction. However, the present invention may be simply used for observation for diagnosis. In this case, it suffices to cause the operator to designate pause cancellation (playback resumption) or as shown in FIG. 10, automatically resume playback when a predetermined period of time (e.g., five sec) elapses after pause (S13 and S14).

In handling an organ with small movement other than an organ with large movement like the heart, it suffices to pause playback at intervals of predetermined imaging angles, e.g., 10°, as shown in FIG. 11, instead of pausing playback depending on a heartbeat signal (S16). This technique can be applied to not only consecutive 2D images but also a stereoscopically constructed image or a three-dimensional image.

In handling image data obtained by, for example, imaging while linearly moving the X-ray tube 112 or the like from the head to the toe, instead of image data to be rotated and displayed, it suffices to pause playback at specific imaging positions on the heart or the like or at predetermined intervals, e.g., 10 cm (S17).

Figure 13:
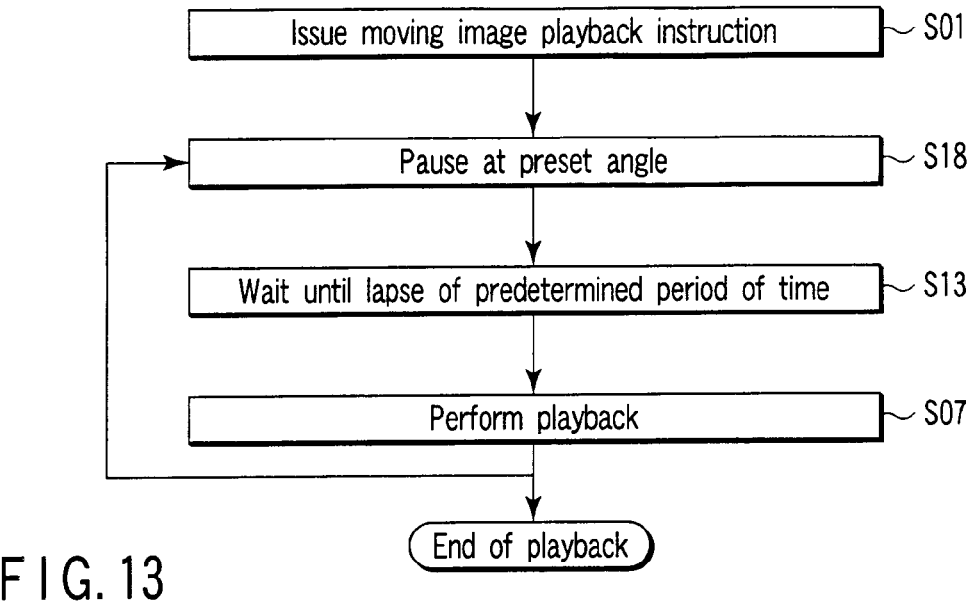
FIG. 13 is a flowchart showing another playback procedure according to this embodiment.

In a routine "check", many hospitals often determine their own observation angles in advance and image all patients from the same observation angles. Each apparatus can store its own observation angle in advance (auto positioning function). As shown in FIG. 13, therefore, if data obtained by rotating imaging contains an image with a preset angle, it suffices to pause playback at the angle (stored in the memory) (S18).

Figure 14:
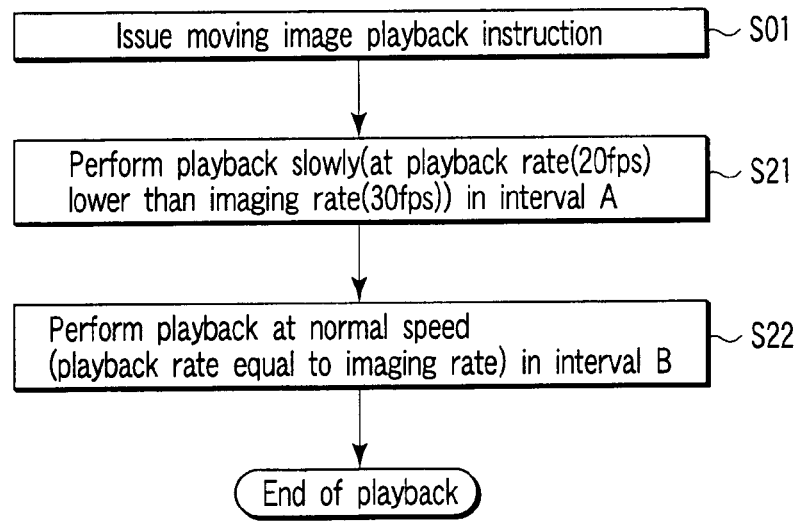
FIG. 14 is a flowchart showing another playback procedure according to this embodiment.

According to the above description, playback is paused in a specific cardiac phase. However, it suffices to decrease (increase) the playback speed (playback frame rate) only in a specific period in a heartbeat to a speed lower (higher) than the imaging frame rate. Assume that an interval A is a period (70 to 100%) including a contraction phase, in which the cardiac motion is relatively large, and an interval B is a period (0 to 69%) including a diastolic phase of the heart, in which the cardiac motion is relatively small and hence is easy to observe, as shown in FIGS. 14 and 15. In the interval A, playback is performed slowly at a rate (e.g., 20 fps) lower than the rate (30 fps) at the time of imaging operation. In the interval B in which the cardiac motion is relatively small, images are played back at 1× speed (S21 and S22). In the interval A in which the cardiac motion is large, images are played back slowly.

Figure 17A:
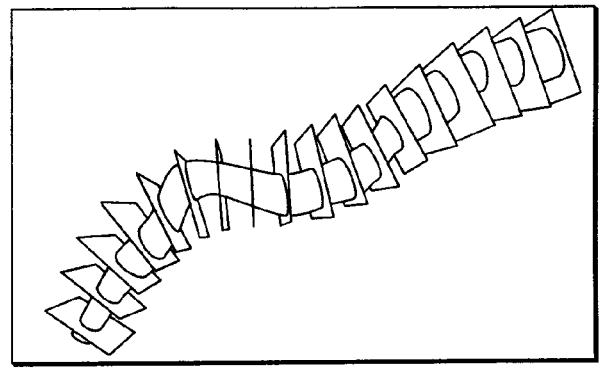
FIGS. 17A and 17B are views showing other image display examples according to this embodiment.
Figure 17B:
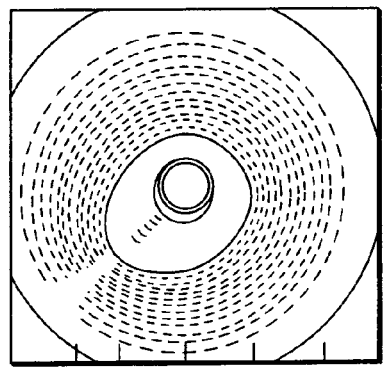

The above description has exemplified the display of the images obtained by the X-ray diagnostic apparatus. However, this embodiment is not limited to the X-ray diagnostic apparatus. For example, as shown in FIGS. 17A and 17B, the embodiment can be applied to the display of images obtained by an intra-vascular ultrasound apparatus (IVUS). The IVUS is generally used to display a plurality of 2D ultrasound images by inserting the IVUS into a blood vessel and moving it at a predetermined speed (e.g., 1 mm/sec), assuming that the acquisition rate is 1 frame/sec. That is, the frames of ultrasound images are made to correspond to the moving distance. As shown in FIGS. 16 and 17A, for example, pausing playback at every 20th frame is equivalent to pausing playback at intervals of 2 cm (S23).

Figure 18:
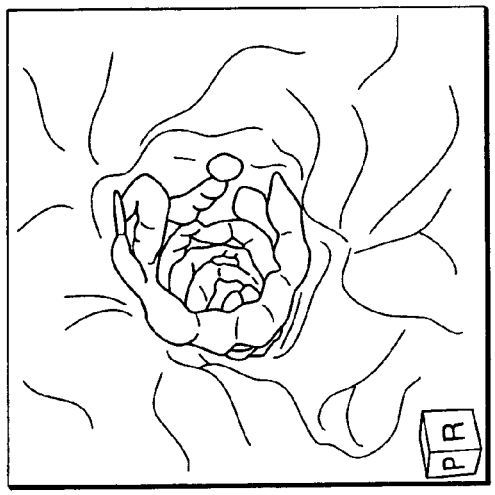
FIG. 18 is a view showing another image display example according to this embodiment.
Figure 19:
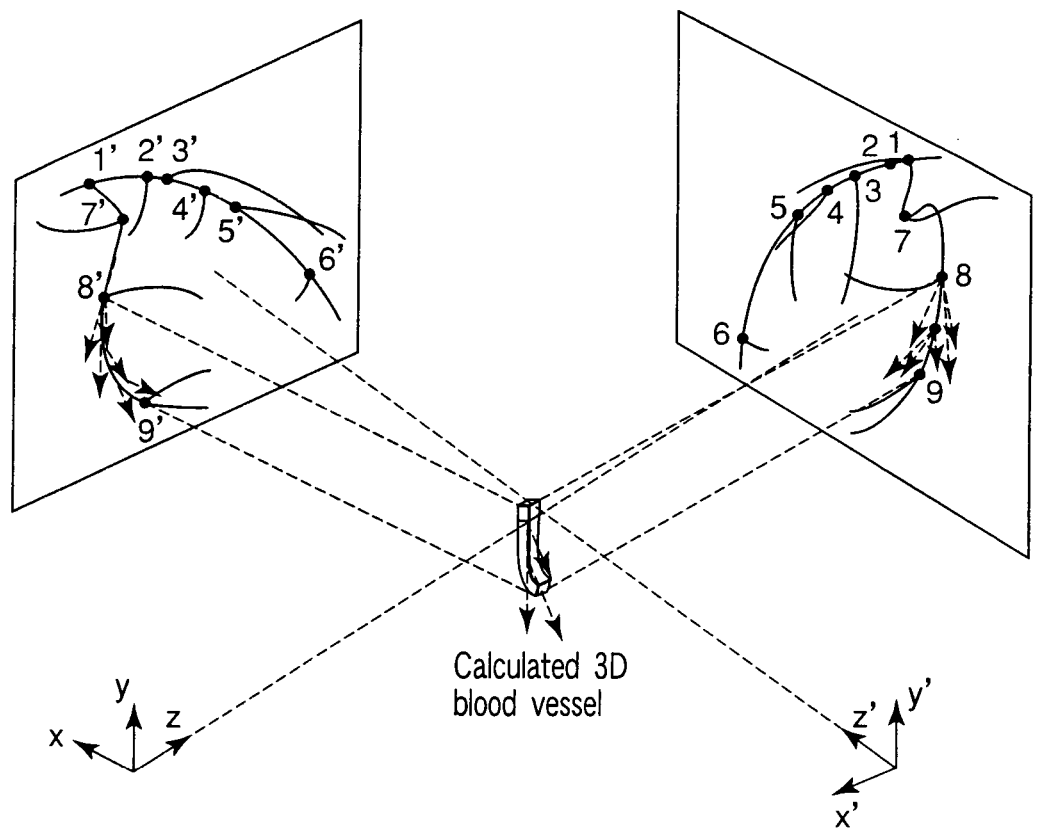
FIG. 19 is a supplementary view for feature point designating operation in the prior art.

Likewise, in so-called fly-through display in which the forward field of view of reconstructed images obtained by X-ray CT or MRI is displayed as a moving image while the viewpoint is moved within a blood vessel as shown in FIG. 18, pausing playback at predetermined distance intervals makes it possible to provide a better sense of distance.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus, comprising:
   a storage unit which stores data of a plurality of medical images at different imaging angles or different imaging positions with respect to a same region of a subject, wherein the plurality of medical image are X-ray images;
   a display which displays the data of a medical image read out from the storage unit;
   a control unit which controls the storage unit and the display to play back said plurality of medical images as moving images in a first loop without pause, to playback said plurality of medical images as moving images in a second loop, and automatically pause playback of the medical images during the second loop, wherein the control unit pauses display of at least two medical images that correspond to a same cardiac phase and exhibit a difference of 90°±10° between the imaging angles;

a designating operation unit which designates anatomically corresponding feature points on the at least two paused medical images; and a determining unit which determines a place to pause based on a predetermined condition, wherein the control unit resumes playing back the medical images in response to a predetermined operation by an operator after pausing playback of the medical images.

2. An apparatus according to claim 1, wherein the control unit resumes playing back the medical images a predetermined period of time after pause of playback of the medical images.

3. An apparatus according to claim 1, wherein the control unit pauses display of a medical image corresponding to the specific cardiac phase.

4. An apparatus according to claim 1, wherein the control unit pauses display of a medical image corresponding to a specific respiratory phase.

5. An apparatus according to claim 1, wherein the control unit pauses display of a medical image at intervals of a predetermined number of frames.

6. An apparatus according to claim 1, wherein the control unit pauses display of a medical image at every specific imaging angle or every specific imaging position.

7. An apparatus according to claim 1, wherein the control unit repeatedly plays back said plurality of medical images in a forward direction.

8. An apparatus according to claim 1, wherein the control unit repeatedly plays back said plurality of medical images in a forward direction and a reverse direction alternately.

9. An apparatus according to claim 1, wherein the control unit resumes playback in response to clicking on a feature point on a paused medical image.

10. An image processing apparatus, comprising:

a storage unit which stores a plurality of medical image data concerning a subject;

a display unit which displays data of a medical image read out from the storage unit; and a control unit which controls the storage unit to playback and display said plurality of medical images as moving images in a first loop without pause, to play-back said plurality of medical images as moving images in a second loop, wherein the control unit pauses, during the second loop, display of at least two medical images that correspond to a same specific cardiac phase and exhibit a difference of 90°±10° between imaging angles, and change a playback frame rate of said plurality of medical images between a frame rate substantially equal to an imaging frame rate and a frame rate lower than the imaging frame rate.

11. An apparatus according to claim 10, wherein the control unit decreases a playback frame rate in a period including a contraction phase of a heart to a frame rate lower than a playback frame rate in another period.

12. An apparatus according to claim 10, wherein the control unit performs playback at a frame rate equal to the imaging frame rate in a period other than a period corresponding to the predetermined rule, and performs playback at a frame rate lower than the imaging frame rate in a period corresponding to the predetermined rule.

13. An apparatus according to claim 12, wherein the control unit returns the playback frame rate to a frame rate equal to the imaging frame rate in response to predetermined operation by an operator after changing the playback frame rate to a frame rate lower than the imaging frame rate.

14. An apparatus according to claim 12, wherein the control unit returns the playback frame rate to a frame rate equal to the imaging frame rate a predetermined period of time after changing the playback frame rate to a frame rate lower than the imaging frame rate.

15. A non-transitory computer-readable storage medium storing a program for causing a computer to perform steps of:

storing data of a plurality of medical images concerning a subject;

displaying data of a medical image read out from the storage unit; and playing back and displaying said plurality of medical images in a first loop without pause, playing back said plurality of medical images as moving images in a second loop, and pausing playback of the medical images during the second loop, the pausing step including pausing display of at least two medical images that correspond to a same specific cardiac phase and exhibit a difference of 90°±10° between imaging angles.

* * * * *